(12) United States Patent
Chen et al.

(10) Patent No.: US 9,062,303 B2
(45) Date of Patent: Jun. 23, 2015

(54) METHODS AND COMPOSITIONS FOR THE RAPID ISOLATION OF SMALL RNA MOLECULES

(75) Inventors: Fuqiang Chen, St. Louis, MO (US); Carol Kreader, St. Louis, MO (US)

(73) Assignee: SIGMA-ALDRICH CO. LLC, St. Louis, MO (US)

( * ) Notice: Subject to any disclaimer, the term of this patent is extended or adjusted under 35 U.S.C. 154(b) by 224 days.

(21) Appl. No.: 12/820,250

(22) Filed: Jun. 22, 2010

(65) Prior Publication Data
US 2010/0256351 A1   Oct. 7, 2010

Related U.S. Application Data

(62) Division of application No. 11/363,982, filed on Feb. 28, 2006, now abandoned.

(51) Int. Cl.
C12Q 1/68   (2006.01)
C12N 15/10   (2006.01)

(52) U.S. Cl.
CPC .......... *C12N 15/1003* (2013.01); *C12Q 1/6806* (2013.01)

(58) Field of Classification Search
None
See application file for complete search history.

(56) References Cited

U.S. PATENT DOCUMENTS

| | | | |
|---|---|---|---|
| 5,155,018 A | 10/1992 | Gillespie et al. | |
| 5,234,809 A | 8/1993 | Boom et al. | |
| 5,972,613 A | 10/1999 | Somack et al. | |
| 5,990,302 A | 11/1999 | Kuroita et al. | |
| 6,037,465 A * | 3/2000 | Hillebrand et al. | 536/25.42 |
| 6,172,192 B1 | 1/2001 | Jacobs et al. | |
| 6,228,643 B1 | 5/2001 | Greenland et al. | |
| 6,383,393 B1 | 5/2002 | Colpan et al. | |
| 6,875,857 B2 | 4/2005 | Simms | |
| 7,074,916 B2 | 7/2006 | Bastian et al. | |
| 7,148,343 B2 | 12/2006 | Bair, Jr. et al. | |
| 7,329,491 B2 | 2/2008 | Kirchgesser et al. | |
| 7,531,308 B2 | 5/2009 | Ray et al. | |
| 2002/0127587 A1 | 9/2002 | Simms et al. | |
| 2003/0204077 A1 | 10/2003 | Simms | |
| 2004/0019196 A1* | 1/2004 | Bair et al. | 536/25.4 |
| 2005/0009036 A1* | 1/2005 | Montesclaros et al. | 435/6 |
| 2005/0054847 A1 | 3/2005 | Madden et al. | |
| 2005/0059024 A1* | 3/2005 | Conrad | 435/6 |
| 2006/0105372 A1 | 5/2006 | Bair et al. | |
| 2007/0015165 A1 | 1/2007 | Chen et al. | |

FOREIGN PATENT DOCUMENTS

| | | | |
|---|---|---|---|
| EP | 0818461 A2 | 1/1998 | |
| EP | 1994142 B1 | 11/2008 | |
| WO | 2004094635 A2 | 11/2004 | |
| WO | 2005012523 A1 | 2/2005 | |
| WO | 2005103252 A1 | 11/2005 | |

OTHER PUBLICATIONS

Ahmad, "Free Energy Changes in Denaturation of Ribonuclease A by Mixed Denaturants", The Journal of Biological Chemistry, 1984, pp. 4183-4186, vol. 259, No. 76.
Brody et al., "History and principles of conductive media for standard DNA electrophoresis", Analytical Biochemistry, 2004, pp. 1-13, vol. 333.
Harada et al., "Application of Combined Reagent Solution to the Oxidative Refolding of Recombinant Human Interleukin 6", Chemical and Pharmaceutical Bulletin, 2001, pp. 1128-1131, vol. 49, No. 9.
Hronowski et al., "Nonspecific interaction of proteoglycans with chromatography media and surfaces: effect of this interaction on the isolation efficiencies", Analytical Biochemistry, 1990, pp. 50-57, vol. 191, No. 1, Abstract only provided, Only Abstract considered.
Kolosova et al., "Isolation of high-quality RNA from gymnosperm and angiosperm trees", BioTechniques, 2004, pp. 821-824, vol. 35.
Oguri, "Electromigration methods for amino acids, biogenic amines and aromatic amines", Journal of Chromatography B, 2000, pp. 1-19, vol. 747.
Pateraki et al., "Isolation of high-quality nucleic acids from *Cistus creticus* ssp. *creticus* and other medicinal plants", Analytical Biochemistry, 2004, pp. 90-92, vol. 328.
Van Dessel et al., "Isolation of high quality RNA from *Streptomyces*", Journal of Microbiological Methods, 2004, pp. 135-137, vol. 58.
Wolff et al., "Cation selective promotion of tubulin polymerization by alkali metal chlorides", Protein Science, 1996, pp. 2020-2028, vol. 5.
International Search Report for PCT/US07/60575, dated Sep. 24, 2007, 1 page.
Non-Final Office Action for U.S. Appl. No. 11/363,982 dated Sep. 26, 2007, 20 pages.
Non-Final Office Action for U.S. Appl. No. 11/363,982 dated May 2, 2008, 13 pages.
Final Office Action for U.S. Appl. No. 11/363,982 dated Dec. 10, 2008, 11 pages.
Non-Final Office Action for U.S. Appl. No. 11/363,982 dated Jul. 2, 2009, 12 pages.
Final Office Action for U.S. Appl. No. 11/363,982 dated Jan. 4, 2010, 16 pages.
Supplementary European Search Report for EP07701244 dated May 26, 2010, 6 pages.
Decision to Grant for European Patent Application No. 07701244.1, mailed Dec. 8, 2011, 1 page.

\* cited by examiner

*Primary Examiner* — Kenneth R. Horlick
*Assistant Examiner* — David Thomas
(74) *Attorney, Agent, or Firm* — Polsinelli PC

(57) ABSTRACT

The present invention provides methods for the rapid and efficient isolation of small RNA from a biological sample. In particular, small RNA is separated and isolated from large RNA, DNA, proteins, and other macromolecules in the biological sample.

23 Claims, No Drawings

METHODS AND COMPOSITIONS FOR THE RAPID ISOLATION OF SMALL RNA MOLECULES

CROSS REFERENCE TO RELATED APPLICATIONS

This application is a divisional application of U.S. patent application Ser. No. 11/363,982, filed on Feb. 28, 2006, which is hereby incorporated by reference in its entirety.

FIELD OF THE INVENTION

The present invention relates to methods, compositions, and kits to isolate small RNA molecules from biological samples.

BACKGROUND OF THE INVENTION

More than a decade ago a non-coding 22-nucleotide (nt) RNA (lin-4) was discovered that played an important role in the developmental timing of *Caenorhabditis elegans*. It was not realized, however, until just a just few years ago that small RNA molecules such as lin-4 are ubiquitous and play important regulatory roles in virtually all eukaryotes. Recent work has shown that prokaryotes and viruses also express small regulatory RNA molecules. Thus, in addition to large RNA molecules, such as messenger RNA (mRNA) and ribosomal RNA (rRNA), cells express an array of small RNA molecules, including 5.8S rRNA, 5S rRNA, transfer RNA (tRNA), small nuclear RNA (snRNA), small nucleolar RNA (snoRNA); micro RNA (miRNA), small interfering RNA (siRNA), trans-acting siRNA (tasiRNA), repeat-associated siRNA (ra-siRNA), small temporary RNA (stRNA), tiny non-coding RNA (tncRNA), small scan RNA (snRNA), and small modulatory RNA (smRNA). Micro RNA molecules, which are processed from larger primary transcripts and range from 20-23 nucleotides in length, have emerged as a hot topic in molecular biology research because of their important roles in a wide range of biological processes, including gene regulation, cell differentiation, growth, and development, as well as certain disease states. Other small RNA molecules, such as siRNAs, are also involved in gene silencing and genome modification.

The long delay to the realization of the existence and importance of small RNA could, in part, be attributed to the fact that small RNA molecules are often unintentionally eliminated because of their small sizes from preparations of natural RNA populations. Furthermore, small RNA molecules represent a very small fraction in terms of weight of the total RNA population, and without removal of abundant RNAs and enrichment of small RNAs, their detection could be severely hampered. Historically, variations of two methods have been used to isolate RNA from biological samples. The first method relies on chemical extraction with organic solvents such as phenol and chloroform under acidic conditions to separate DNA and other biomolecules from the RNA, which is then concentrated by alcohol precipitation. Alcohol precipitation, however, does not quantitatively recover small RNA molecules. The second method relies on immobilization of RNA on a solid support binding matrix, such as silica. For this, the RNA-containing sample is mixed with a high salt solution or a salt and alcohol mixture to decrease the affinity of RNA for water and increase its affinity for the silica matrix. Small RNA, however, binds poorly to the support matrix under the conditions routinely used. Thus, most existing RNA preparation methods and commercial RNA purification kits are deficient in capturing small RNA.

With the recent surge of interest in miRNA and other small RNA molecules, the standard isolation procedures have been modified to facilitate the isolation of small RNA. These methods largely rely on phenol and chloroform extraction and step-wise alcohol fractionation. For example, U.S. Publication No. 2005/0059024 discloses a method in which a cell lysate is extracted with phenol and chloroform to partition the genomic DNA into an interphase between an organic lower phase and an aqueous upper phase. The aqueous upper phase is collected and mixed with a low percentage of alcohol and applied to a first binding matrix. The large RNA is immobilized onto the first matrix and the small RNA flow through the matrix. The flow-through fraction is then mixed with a higher percentage of alcohol and applied to a second binding matrix, to which the small RNA binds and can be recovered. Thus, small RNA can be isolated and purified using a multi-step procedure. A major drawback of the current methodology is the use of phenol and chloroform, not only because they pose potential health hazards but also because they are ineffective with certain biological material, such as plant tissues that are rich in phenolic or polyphenolic compounds. Another drawback of the current methodology is that phase separation and alcohol fractionation are laborious and time consuming, making them incompatible with high throughput and automation demands.

The present invention provides methods and compositions for the rapid isolation of small RNA from a variety of biological sources without using phenol and chloroform extraction or alcohol gradient fractionation.

SUMMARY OF THE INVENTION

Among the various aspects of the invention is the provision of a method for isolating small RNA from a biological sample. The method comprises contacting the biological sample with a chaotropic agent and a metal salt such that the small RNA is released from the debris in the biological sample and a solution of soluble small RNA is formed. The method further comprises contacting the solution of soluble small RNA with a chromatographic binding matrix and at least one alcohol, wherein the small RNA binds to the chromatographic binding matrix. Lastly, the method comprises eluting the small RNA from the chromatographic binding matrix, thereby isolating the small RNA.

Other aspects and features of the invention will be in part apparent and in part described in more detail herein.

DETAILED DESCRIPTION OF THE INVENTION

It has been discovered that contacting a biological sample with a chaotropic agent and a metal salt leads to the release of small RNA from other biomolecules. In particular, contact with the chaotropic agent and metal salt selectively precipitates the large RNA, genomic DNA, and other large macromolecules, whereas the small RNA remains in solution. The small RNA may be readily separated and isolated from the aggregated macromolecules. As illustrated in the examples, the methods and compositions of the present invention allow the rapid isolation of pure preparations of small RNA in high yield from a variety of organisms, including, plant tissue, mammalian cultured cells, mammalian tissue, yeast cells, and bacterial cells.

I. Extraction Compositions

One aspect of the invention encompasses an extraction composition. Typically the extraction composition will have a chaotropic agent and a metal salt. In this context, the term "composition" is used in its broadest sense to mean use of a chaotropic agent and metal salt for the separation of small RNA from a biological sample. The term composition does not mean that the two agents have to be contacted with the biological sample at the same time as a part of the same solution. It is contemplated for example, as described below, that the chaotropic agent and metal salt may be contacted with the biological sample either simultaneously as part of the same mixture or added sequentially, one reagent after the other. As will be appreciated by a skilled artisan, the extraction composition may optionally include a variety of other agents without departing from the scope of the invention. Suitable non-limiting examples of agents comprising the extraction composition are detailed below.

(a) Chaotropic Agent

A variety of chaotropic agents are suitable for use in the extraction composition. Generally speaking, the chaotropic agent denatures proteins, disrupts membranes, releases nucleic acids, protects RNA from degradation, and facilitates cell lysis. Examples of suitable chaotropic agents include guanidine hydrochloride, guanidine thiocyanate, guanidine carbonate, sodium iodide, sodium perchlorate, sodium trichloroacetate, urea, and thiourea. The chaotropic agent may be incorporated into the extraction composition alone or as a combination of two or more chaotropic agents. As will be appreciated by one skilled in the art, the choice of chaotropic agent will be determined by the origin of material from which small RNA is to be isolated. In one embodiment, the chaotropic agent is guanidine thiocyanate. Guanidine thiocyanate, however, is not particularly suitable for RNA isolation from certain plant tissues, such as cotton leaves, grape leaves, red maple leaves, and gymnosperm conifer needles, which are rich in phenolic or polyphenolic compounds. In another embodiment, the chaotropic agent is a combination of two or more quanidinium salts. In a preferred embodiment, the chaotropic agent is guanidine hydrochloride.

The concentration of the chaotropic agent or the combination of chaotropic agents in the extraction composition may and will vary but may range from about 1 M to about 8 M. Lower concentrations of a chaotropic agent may be used if cell disruption and RNase inhibition are not major concerns. In one aspect, the concentration of the chaotopic agent is about 3 M. In another aspect, the concentration of the chaotopic agent is about 6 M. In another aspect, the concentration of the chaotopic agent is about 4 M. In yet another aspect, the concentration of the chaotopic agent is about 5 M.

(b) Metal Salt

The extraction composition includes at least one metal salt. A variety of metal salts are suitable for use in the invention. The metal salt may be incorporated into the extraction composition before or after contacting the biological sample. The metal salt may be a group IA metal salt or a group IIA metal salt. Suitable examples of group IIA metals include beryllium, magnesium, calcium, strontium, and barium. Suitable examples of group IA metals include lithium, sodium, potassium cesium, and francium. In a preferred embodiment, the metal salt is a lithium salt. Examples of suitable lithium salts include lithium acetate, lithium borate, lithium carbonate, lithium chloride, and lithium citrate. In a preferred embodiment, the lithium salt is lithium chloride.

The concentration of metal salt or combination of metal salts may range from about 1 M to about 8 M. In one aspect, the concentration of lithium salt ranges from about 1.5 M to about 6 M. In one embodiment, the concentration of lithium chloride is about 6 M. In another embodiment, the concentration of lithium chloride is about 2.4 M. In another embodiment, the concentration of lithium chloride is about 1.8 M. In yet another embodiment, the concentration of lithium chloride is about 3.6 M.

Without being bound by any particular theory, it is believed that the combination of a chaotropic agent and a lithium salt in the extraction composition creates a discriminating environment that is particularly suitable for the separation of large RNA from small RNA. It is known that $Li^+$ ions have a very high charge/radius ratio and a unique affinity for RNA molecules. They can effectively neutralize the negative charges on the RNA backbone and remove much of the water shell from the RNA molecule. A chaotrope, on the other hand, has a strong disrupting ability, which can keep the charge-neutralized RNA molecules from collapsing on each other and becoming aggregated. As a result of the counteraction, each charge-neutralized RNA molecule may behave as a discrete entity in the extraction composition. It is further believed that charge-neutralized large RNAs possess a higher density than the extraction composition and, therefore, they are very susceptible to precipitation, whereas charge-neutralized small RNAs have a lower density than the extraction composition and, therefore, they substantially remain in solution. The density of each RNA molecule may also be affected to some extent by pH, for $H^+$ can compete with $Li^+$ for the negative charges on the RNA backbone. As a consequence, the extraction composition is optimized for extracting small RNA, as detailed below.

(c) pH and Buffer

It has been discovered, as detailed in the examples, that the pH of the extraction composition differentially affects the solubility of small RNA, large RNA, and genomic DNA. At values below about pH 4, large RNA and genomic DNA are insoluble and precipitate out of solution, whereas the small RNA is substantially soluble and stays in solution. As pH values rise above about pH 4, the small RNA remains soluble and the large RNA remains insoluble, but the solubility of DNA increases.

In order to maintain a desired pH for optimizing small RNA isolation, therefore, a buffer is typically incorporated into the extraction composition. In one embodiment, the pH of the extraction composition ranges from about 3 to about 8. In an alternative embodiment, the extraction composition has a pH of about 7. In another embodiment, the pH of the extraction composition is less than about 5.0 and more preferably, is less than about 4.0. In an alternative embodiment, the extraction composition has a pH that ranges from about 3.0 to about 4.0. In yet another embodiment, the extraction composition has a pH of about 3.5.

A variety of buffers are suitable for use in the extraction composition. By way of non-limiting example, the buffers may include, but are not limited to, trizma acetate, EDTA, tris, glycine, and citrate. EDTA also has the ability to chelate $Mg^{2+}$ ions, thereby inactivating nucleases. In one aspect, the buffer is EDTA. In a preferred aspect, the buffer is trizma acetate. The buffer may be incorporated into the extraction composition alone or as a combination of two or more buffers. The concentration of buffer is typically sufficient to maintain a desired pH range. In one embodiment, the concentration of buffer in the extraction composition may range from about 20 mM to about 100 mM. In other embodiment, the concentration of the buffer in the extraction composition may range from about 30 mM to about 50 mM. In a further embodiment, the concentration of buffer in the extraction composition is about 40 mM.

(d) Detergent

The extraction composition may optionally include one or more detergents. A variety of detergents may be utilized in the present invention. Generally speaking, the detergent will typically promote protein solubilization, membrane disruption, and cell permeabilization. Detergents are preferably included in certain embodiments when small RNA is separated from certain plant tissues that are rich in phenolic or polyphenolic compounds. Examples of such plant tissues may include, but are not limited to, cotton leaves, grape leaves, red maple leaves, and gymnosperm conifer needles.

Examples of suitable detergents that may be incorporated into the extraction composition are polyoxyethylene detergents and quaternary ammonium compounds. Polyoxyethylene detergents are nonionic, while quaternary ammonium compounds are cationic. Non-limiting examples of polyoxyethylene detergents include polyoxyethylenesorbitan monolaurate (Tween 20, Sigma-Aldrich, St. Louis, Mo.), polyoxyethylenesorbitan monooleate (Tween 80, Sigma-Aldrich, St. Louis, Mo.), octylphenoxy poly(ethyleneoxy) ethanol (Igepal CA 630, Sigma-Aldrich, St. Louis, Mo.), and t-octylphenoxypolyethoxyethanol (Triton X100 and Triton X114, Sigma-Aldrich, St. Louis, Mo.), and P-40 (NP-40, Sigma-Aldrich, St. Louis, Mo.). Non-limiting examples of quaternary ammonium compounds include hexadecyltrimethylammonium bromide (CTAB, Sigma-Aldrich, St. Louis, Mo.), dodecyltrimethylammonium bromide, ethylhexadecyldimethylammonium bromide, benzethonium chloride (Hyamine 1622, Sigma-Aldrich, St. Louis, Mo.), and benzyldimethylhexadecylammonium chloride. The detergents may be incorporated in the extraction composition alone or as a combination of two or more detergents. In one embodiment, the detergent is Triton X100. In another embodiment, the detergent is Igepal. In a preferred embodiment, the detergent is Tween 20.

As will be appreciated by a skilled artisan, the concentration of detergent present in the extraction composition can and will vary. In one embodiment, the detergent concentration is between about 0.1% to about 10% by weight. In another embodiment, the detergent concentration is between about 1% and about 5% by weight. In still another embodiment, the detergent concentration is between about 1% and about 2% by weight.

(e) Thiol-Reducing Agent

The extraction composition may also comprise a thiol-reducing agent to block the formation of disulfide bonds upon cell disruption and protein denaturation, thereby keeping endogenous RNases inactive. Suitable thiol-reducing agents include dithiothreitol (DTT), 2-mercaptoethanol, 2-mercaptoethylamine, and tris(carboxyethyl)phosphine (TCEP). In one embodiment, the thiol-reducing agent is DTT, with a concentration between about 1 mM and about 10 mM. In another aspect, the thiol-reducing agent is 2-mercaptoethanol. In one embodiment, the concentration of 2-mercaptoethanol is between about 0.1% to about 2% by weight. In yet another aspect, the concentration of 2-mercaptoethanol is about 1% by weight.

(f) Antifoaming Agent

Depending upon the source of the biological sample, an antifoaming agent may optionally be incorporated into the extraction composition. Antifoaming agents may be an organic antifoaming agent or a silicone-based antifoaming agent. Examples of organic antifoaming agents include Antifoam 204 and Antifoam O-30. Examples of silicone-based antifoaming agents include Antifoam A, Antifoam B, Antifoam C, Antifoam Y-30, and Sag 471. The concentration of antifoam agent is typically sufficient to ensure adequate defoaming. The concentration of an organic antifoam agent may be within the range from 0.005% to 0.01% by weight. The concentration of a silicone-based agent may be within the range from 1 ppm to 100 ppm.

(g) Bulking Agent

A bulking agent may optionally be incorporated into the extraction composition to facilitate the precipitation of nucleic acids. Bulking agents typically selectively promote the precipitation of large nucleic acids compared to small nucleic acids. In one embodiment, a bulking agent may be added to the extraction composition to promote the precipitation of large RNA and genomic DNA. In another embodiment, a bulking agent may be added to the extraction composition to discriminate between the different sized molecules of small RNA.

Several bulking agents are suitable for use in the present invention. A bulking agent may be nonionic or ionic. Nonionic bulking agents include alcohols and hydrophilic neutral polymers. Exemplary alcohols that may be used as nonionic bulking agents include butanol, ethanol, isopropanol, methanol, and propanol. Hydrophilic neutral polymers that may be used as nonionic bulking agents include dextran sulfate, polyethylene glycol (PEG), tetraethylene glycol, and polyvinylpyrrolidine (PVP). The concentration of a nonionic bulking agent or the combination of nonionic agents may range from about 3% to about 10% by weight. Ionic bulking agents include cationic detergents and polyamines. Examples of ionic bulking agents include hexadecyltrimethylammonium bromide (CTAB), dodecyltrimethylammonium bromide, spermine, and spermidine. Other polyamines, or their derivatives, and other cationic detergents also may be used as ionic bulking agents. The concentration of an ionic bulking agent or the combination of ionic agents may range from about 10 mM to about 100 mM, but other concentrations also may be useful. In one aspect, the bulking agent is the nonionic agent, isopropanol. In another aspect, the nonionic bulking agent ethanol is incorporated into the extraction composition. In yet another aspect, the ionic bulking agent spermidine is incorporated into the extraction composition.

The extraction compositions of the invention include any combination of chaotropic agents and metal salts detailed herein. The extraction composition may optionally include, in addition to the chaotropic agent and metal salt, any of the buffers, detergents, thiol-reducing agents, antifoaming agents, bulking agents detailed herein or otherwise known in the art to be useful to isolate small RNA from a biological sample. Non-limiting examples of extraction compositions of the invention are detailed in Table A. Suitable examples of extraction compositions of the invention detailed in Table A include the listed chaotropic agent and a metal salt and optionally include any of the agents listed as "other agents".

TABLE A

| Chaotropic agent | Metal salt | Other agents |
|---|---|---|
| guanidine hydrochloride | lithium chloride | buffer, detergent, thiol-reducing agent, antifoaming agent, bulking agent |
| guanidine hydrochloride | lithium acetate | buffer, detergent, thiol-reducing agent, antifoaming agent, bulking agent |
| guanidine hydrochloride | lithium borate | buffer, detergent, thiol-reducing agent, antifoaming agent, bulking agent |
| guanidine hydrochloride | lithium carbonate | buffer, detergent, thiol-reducing agent, antifoaming agent, bulking agent |
| guanidine hydrochloride | lithium citrate | buffer, detergent, thiol-reducing agent, antifoaming agent, bulking agent |

TABLE A-continued

| Chaotropic agent | Metal salt | Other agents |
|---|---|---|
| guanidine thiocyanate | lithium chloride | buffer, detergent, thiol-reducing agent, antifoaming agent, bulking agent |
| guanidine thiocyanate | lithium acetate | buffer, detergent, thiol-reducing agent, antifoaming agent, bulking agent |
| guanidine thiocyanate | lithium borate | buffer, detergent, thiol-reducing agent, antifoaming agent, bulking agent |
| guanidine thiocyanate | lithium carbonate | buffer, detergent, thiol-reducing agent, antifoaming agent, bulking agent |
| guanidine thiocyanate | lithium citrate | buffer, detergent, thiol-reducing agent, antifoaming agent, bulking agent |
| guanidine carbonate | lithium chloride | buffer, detergent, thiol-reducing agent, antifoaming agent, bulking agent |
| guanidine carbonate | lithium acetate | buffer, detergent, thiol-reducing agent, antifoaming agent, bulking agent |
| guanidine carbonate | lithium borate | buffer, detergent, thiol-reducing agent, antifoaming agent, bulking agent |
| guanidine carbonate | lithium carbonate | buffer, detergent, thiol-reducing agent, antifoaming agent, bulking agent |
| guanidine carbonate | lithium citrate | buffer, detergent, thiol-reducing agent, antifoaming agent, bulking agent |
| sodium iodide | lithium chloride | buffer, detergent, thiol-reducing agent, antifoaming agent, bulking agent |
| sodium iodide | lithium acetate | buffer, detergent, thiol-reducing agent, antifoaming agent, bulking agent |
| sodium iodide | lithium borate | buffer, detergent, thiol-reducing agent, antifoaming agent, bulking agent |
| sodium iodide | lithium carbonate | buffer, detergent, thiol-reducing agent, antifoaming agent, bulking agent |
| sodium iodide | lithium citrate | buffer, detergent, thiol-reducing agent, antifoaming agent, bulking agent |
| sodium perchlorate | lithium chloride | buffer, detergent, thiol-reducing agent, antifoaming agent, bulking agent |
| sodium perchlorate | lithium acetate | buffer, detergent, thiol-reducing agent, antifoaming agent, bulking agent |
| sodium perchlorate | lithium borate | buffer, detergent, thiol-reducing agent, antifoaming agent, bulking agent |
| sodium perchlorate | lithium carbonate | buffer, detergent, thiol-reducing agent, antifoaming agent, bulking agent |
| sodium perchlorate | lithium citrate | buffer, detergent, thiol-reducing agent, antifoaming agent, bulking agent |
| sodium trichloroacetate | lithium chloride | buffer, detergent, thiol-reducing agent, antifoaming agent, bulking agent |
| sodium trichloroacetate | lithium acetate | buffer, detergent, thiol-reducing agent, antifoaming agent, bulking agent |
| sodium trichloroacetate | lithium borate | buffer, detergent, thiol-reducing agent, antifoaming agent, bulking agent |
| sodium trichloroacetate | lithium carbonate | buffer, detergent, thiol-reducing agent, antifoaming agent, bulking agent |
| sodium trichloroacetate | lithium citrate | buffer, detergent, thiol-reducing agent, antifoaming agent, bulking agent |
| urea | lithium chloride | buffer, detergent, thiol-reducing agent, antifoaming agent, bulking agent |
| urea | lithium acetate | buffer, detergent, thiol-reducing agent, antifoaming agent, bulking agent |
| urea | lithium borate | buffer, detergent, thiol-reducing agent, antifoaming agent, bulking agent |
| urea | lithium carbonate | buffer, detergent, thiol-reducing agent, antifoaming agent, bulking agent |
| urea | lithium citrate | buffer, detergent, thiol-reducing agent, antifoaming agent, bulking agent |
| thiourea | lithium chloride | buffer, detergent, thiol-reducing agent, antifoaming agent, bulking agent |
| thiourea | lithium acetate | buffer, detergent, thiol-reducing agent, antifoaming agent, bulking agent |
| thiourea | lithium borate | buffer, detergent, thiol-reducing agent, antifoaming agent, bulking agent |
| thiourea | lithium carbonate | buffer, detergent, thiol-reducing agent, antifoaming agent, bulking agent |
| thiourea | lithium citrate | buffer, detergent, thiol-reducing agent, antifoaming agent, bulking agent |

II. Methods for Isolating Small RNA

The extraction compositions of the present invention may be utilized to isolate small RNA molecules from a biological sample. Typically, small RNA molecules are less than about 200 nucleotides in length. Both prokaryotic and eukaryotic cells contain a plurality of different sized RNA molecules. RNA molecules with lengths greater than about 200 nucleotides include messenger RNA (mRNA), 16S/18S ribosomal RNA (rRNA), and 23S/28S rRNA. Small RNA molecules with lengths less than about 200 nucleotides include 5.8S rRNA, 5S rRNA, transfer RNA (tRNA), small nuclear RNA (snRNA), small nucleolar RNA (snoRNA); micro RNA (miRNA), small interfering RNA (siRNA), trans-acting siRNA (tasiRNA), repeat-associated siRNA (rasiRNA), small temporal RNA (stRNA), tiny non-coding RNA (tncRNA), small scan RNA (snRNA), and small modulatory RNA (smRNA).

In the isolation method of the invention, the biological sample is contacted with any of the extraction compositions disclosed herein. Generally speaking, the extraction composition will comprise a chaotropic agent and a metal salt. The biological sample may be contacted with the chaotropic agent and the metal salt simultaneously. Alternatively, the biological sample may contacted with the chaotropic agent and the metal salt sequentially, one reagent after the other. Contact with the extraction composition releases the small RNA from the debris present in the biological sample, such as the large biomolecules, which become insoluble and precipitate out of solution. The precipitated molecules include large RNA, genomic DNA, and other macromolecules, (i.e., collectively referred to as "debris"). The small RNA remains substantially soluble in the extraction composition.

Small RNA may be isolated from a variety of biological samples. Examples of a suitable biological sample include a cell, a tissue from a multicellular organism, a whole organism, a virus, a body fluid, such as serum, blood, saliva, urine, or cerebrospinal fluid, or any other nucleic acid-containing preparation.

As will be appreciated by a skilled artisan, the biological sample may be contacted with the extraction composition by several suitable methods generally known in the art. In one embodiment, cells are lysed upon contact with the extraction composition. In another embodiment, tissue is ground to a fine powder in liquid nitrogen and then mixed with the extraction composition. In another embodiment, tissue is homogenized in the extraction composition in a rotor-stator homogenizer, a pestle-type homogenizer, or a blender. In yet another embodiment, fungal or bacterial cells are chemically treated with enzymes or physically pulverized with beads to disrupt the cell wall prior to being contacted with the extraction composition. In a further embodiment, a nucleic acid-containing preparation is contacted with the extraction composition. In general, contact with the extraction composition causes the selective denaturation and aggregation of the large biomolecules and the formation of debris in the mixture. The small RNA, however, remains in solution and may be separated from the debris and purified from the mixture.

Separation of the small RNA may be accomplished by several methods well known in the art. In one embodiment, the aggregated debris is separated from the small RNA-containing mixture by centrifugation. In another embodiment, the aggregated debris is separated from the small RNA-containing mixture by filtration. In another embodiment, the small RNAs are separated from the debris by chromatography. In an exemplary embodiment, the debris is removed by centrifugation and filtration, and the small RNA is isolated from the soluble mixture by chromatography.

Suitable examples of chromatographic methods include size exclusion chromatography and affinity chromatography. In a preferred embodiment, the small RNAs are isolated by affinity chromatography. Examples of suitable affinity binding matrices include any solid matrix, as well as any coated surface to which nucleic acids bind. In one embodiment, the binding matrix is a hydrophilic matrix. The hydrophilic matrix may be an organic binding matrix or an inorganic binding matrix. Examples of suitable organic hydrophilic matrices include, but are not limited to, acrylic copolymers, cellulose, dextran, agarose, and acrylic amide. Suitable examples of inorganic hydrophilic matrices include, but are not limited to, silica, borosilicate, diatomaceous earth, aluminum oxides, glass, titanium oxides, zirconium oxides, and hydroxyapatite. In one embodiment, the binding matrix is a silica-based binding matrix. Examples of silica matrices include, but are not limited to, silica particles, silica filters, and magnetized silica. In a preferred embodiment, the binding matrix is a filter comprising borosilicate fibers.

Small RNA typically binds to silica-based binding matrices in the presence of a chaotropic salt and a high concentration of alcohol. Alcohols that may be added to the small RNA-containing mixture, to facilitate the binding of small RNA to the binding matrix, include ethanol, isopropanol, butanol, methanol, and propanol. The alcohols may be used alone or in combination of two or more alcohols. In one embodiment, the alcohol added to the binding mixture is ethanol. In other embodiment, the alcohol added to the binding mixture is isopropanol. The concentration of the alcohol or combination of two or more alcohols in the binding mixture is preferentially greater than about 50%. In one aspect, the concentration of ethanol in the binding mixture is about 67%. In another aspect, the concentration of ethanol in the binding mixture is about 55%. Upon binding of the small RNA to the silica or borosilicate binding matrix, impurities are removed with high salt wash solutions and alcohol wash solutions. Examples of high salt wash solutions include, but are not limited to, 12 M LiCl and 9 M LiCl. Examples of alcohol wash solutions include, but are not limited to, 100% ethanol and 80% ethanol. Small RNAs are eluted from the binding matrix with RNase-free water or an RNase-free low salt buffer.

III. Kits for Isolating Small RNA

The extraction composition and the method of the present invention may be combined to create a kit for the isolation of small RNA. In one embodiment, the kit comprises solutions to prepare an extraction composition of the invention and instructions for use. In a preferred embodiment, the kit comprises solutions to prepare an extraction composition of the invention, concomitant additive agents, a separation means, companion wash and elution solutions, and complete instructions for isolating the small RNA. In an exemplary embodiment, the separation means provided in the complete kit is a binding filter comprising borosilicate fibers.

DEFINITIONS

The term "biological sample" as used herein refers to any nucleic acid-containing material derived from any source, either in vivo or in vitro. The biological sample may be a eukaryotic or a prokaryotic cell, a tissue from a multicellular organism, a whole organism, a virus, a body fluid, such as serum, blood, saliva, urine, semen, or cerebrospinal fluid, or a mixture of nucleic acids generated in vitro.

The terms "biomolecules" or "macromolecules" used herein refer to large RNA, DNA, proteins, carbohydrates, lipids, and combinations thereof.

The term "bulking agent" used herein refers to a compound that effectively increases the concentration of nucleic acids because the nucleic acids are excluded from the space occupied by the bulking agent.

The term "chaotropic agent" refers to an agent that disrupts the secondary or higher structure of certain molecules, such that the molecule unfolds and loses biological activity.

The term "debris" used herein refers to the insoluble RNA, DNA, and other biomolecules that precipitate or aggregate upon contact with the extraction composition.

The term "extraction" refers to the release from or the separation of a specific molecule from a mixture of molecules. More specifically, it refers to the process by which small RNA is released from other biomolecules upon contact with the extraction composition, due to the precipitation of the biomolecules upon contact with the extraction composition.

The term "immobilization" refers to adherence or binding of the target molecule (i.e., small RNA) to a binding matrix.

The terms "isolate", "purify", or "separate" refer to the removal of at least a portion of the small RNA from at least part of the debris in a biological sample.

The term "lyse" or "lysis" refers to the rupturing of the cell wall and/or cell membrane of a cell so that cellular contents are released.

The term "small RNA" used herein refers to RNA molecules with lengths of less than about 200 nucleotides. Small RNA molecules may be single stranded or double stranded. Examples of small RNA include, but are not limited to, 5.8 S rRNA, 5 S rRNA, transfer RNA (tRNA), small nuclear RNA (snRNA), small nucleolar RNA (snoRNA); micro RNA (miRNA), small interfering RNA (siRNA), trans-acting siRNA (tasiRNA), repeat-associated siRNA (rasiRNA), small temporal RNA (stRNA), tiny non-coding RNA (tncRNA), small scan RNA (snRNA), and small modulatory RNA (smRNA).

As various changes could be made in the above compounds, products and methods without departing from the scope of the invention, it is intended that all matter contained in the above description and in the examples given below, shall be interpreted as illustrative and not in a limiting sense.

EXAMPLES

The following examples illustrate the invention.

Example 1

Effects of pH on Nucleic Acid Separation

Nine basal solutions were prepared that each comprised 7 M guanidine hydrochloride, 60 mM trizma acetate, and 2% Tween 20, but each had a different pH through titration with acetic acid or NaOH. The pH values were 3.2, 3.4, 3.6, 3.8, 4.0, 5.0, 6.0, 7.0, and 8.0. Nine lysis solutions were prepared by combining each of the nine basal solutions with a 12 M LiCl solution in a 7:3 ratio. The resulting lysis solutions each comprised 4.9 M guanidine hydrochloride, 3.6 M LiCl, 42 mM trizma acetate, and 1.4% Tween 20, and each solution had a different pH. Each lysis solution was further supplemented with 2-mercaptoethanol at 1%.

Grape leaves were ground to a fine powder in liquid nitrogen and nine 100-mg aliquots were prepared from the powdered material. Each aliquot was lysed in 750 µl al of a lysis solution at 55° C. for 4 minutes. The samples were then centrifuged for 5 minutes performed. The supernatant fraction was filtered through a filtration column (C 6866, Sigma-Aldrich, St. Louis, Mo.) by 1 minute of centrifugation to remove carry-over particulates. The clarified lysate was mixed with 830 µl of 100% ethanol and applied to a silica filter binding column (C6991, Sigma-Aldrich, St. Louis, Mo.) in two loadings, with 30 seconds of centrifugation after each loading. The column was washed in succession with 500 µl of 100% ethanol, 500 µl of 12 M LiCl, and twice with 500 µl of an alcohol wash solution comprising 80% ethanol and 10 mM tris (pH 7.0). Each wash step was carried out with a short centrifugation (30 seconds or 1 minute). The column was dried by 1 minute of centrifugation and the bound nucleic acids were eluted in 50 µl of RNase-free water and 1 minute of centrifugation. All centrifugation steps were performed in a bench-top microcentrifuge at top speed (14,000×g) at room temperature. The samples were analyzed by reading the UV absorbance in a spectrophotometer and electrophoresing 0.5 µg of each sample on a 2% agarose gel.

The amount of RNA recovered under each lysis condition is presented in Table 1. The $A_{260/280}$ ratios were between 2.1 and 2.2 for each sample. Following agarose gel electrophoresis, no bands of 18S and 25S rRNA were detected in any of the samples. A strong band of small RNA with a mobility similar to a yeast tRNA standard (70-80 nucleotides) was detected in all samples. Some minor bands of small RNA with mobilities slightly slower than the strong band of small RNA were detectable in the samples prepared with the lysis solutions at pH below 3.8. A genomic DNA band with a mobility slower than a 10 kb DNA marker was detected in the samples prepared with the lysis solutions at pH above 4. The intensity of this genomic DNA band increased as the lysis solutions became more basic. The results indicated that large RNA was in an insoluble form in the lysis solutions regardless of pH and was removed from all preparations, and that samples prepared with the lysis solutions at pH 4 or lower consisted primarily of small RNA and were substantially free of genomic DNA.

TABLE 1

Effect of pH on Yield.

| Condition | Yield |
| --- | --- |
| pH 3.2 | 12.8 µg |
| pH 3.4 | 11.8 µg |
| pH 3.6 | 11.9 µg |
| pH 3.8 | 12.0 µg |
| pH 4.0 | 9.2 µg |
| pH 5.0 | 7.4 µg |
| pH 6.0 | 7.4 µg |
| pH 7.0 | 7.9 µg |
| pH 8.0 | 8.7 µg |

Example 2

Effects of a Nonionic Bulking Agent

A basal solution was prepared comprising 7 M guanidine hydrochloride, 2% Tween 20, and 60 mM trizma acetate, pH 3.4. The basal solution was then combined with a 12 M LiCl solution and ethanol in some formulations in different ratios to form 6 lysis solutions, as detailed in Table 2. Each lysis solution was further supplemented with 2-mercaptoethanol at 1%.

TABLE 2

Composition of Lysis Solutions.

| Solution # | Basal Solution | LiCl Solution | Ethanol |
| --- | --- | --- | --- |
| 1 | 80% | 20% | — |
| 2 | 74% | 20% | 6% |
| 3 | 70% | 20% | 10% |
| 4 | 70% | 30% | — |
| 5 | 64% | 30% | 6% |
| 6 | 60% | 30% | 10% |

Grape leaf samples (100 mg each) were prepared as described above. Each sample was lysed in 750 µl of a lysis solution at 55° C. for 4 minutes. Small RNA was purified as described in Example 1. The samples were analyzed by reading the UV absorbance in a spectrophotometer and running 0.5 µg of each sample on a 4% agarose gel.

The amount of RNA recovered under each lysis condition is presented in Table 3. The $A_{260/280}$ ratios were between 2.1 and 2.2 for each sample. Following agarose gel electrophoresis, no bands of 18S and 25S rRNA or genomic DNA were detected in any of the samples. A very strong band of RNA with a mobility similar to a tRNA standard (70-80 nucleotides) was present in all samples. In addition, two minor bands of small RNA with mobilities slightly slower than the major band of small RNA were detected in the samples that were prepared with Lysis Solutions #1 and #4, which did not contain ethanol as an additive. These two minor bands of small RNA are most likely 5S rRNA (about 120 nucleotides) and 5.8S rRNA (about 150 nucleotides). The intensity of these minor bands were greatly reduced in the samples that were prepared with Lysis Solutions #2 and #5, which contained 6% ethanol as an additive, and they were further reduced to nearly undetectable levels in the samples prepared with Lysis Solution #3 and #6, which contained 10% ethanol as an additive. The results demonstrated that ethanol may be used as a nonionic additive in the process of the present invention to discriminate among different sized molecules of small RNA.

TABLE 3

Effects of Ethanol on Yield.

| Sample # | Yield |
|---|---|
| 1 | 12.2 μg |
| 2 | 8.5 μg |
| 3 | 5.9 μg |
| 4 | 11.6 μg |
| 5 | 9.3 μg |
| 6 | 6.1 μg |

Example 3

Effects of an Ionic Bulking Agent

A lysis solution was prepared comprising 7.2 M guanidine hydrochloride, 2% Tween 20, and 50 mM trizma acetate, pH of 7.0. The lysis solution was further supplemented with 2-mercaptoethanol at 1%. A mouse liver tissue sample (30 mg) was homogenized in 300 μl of the lysis solution with a rotor-stator homogenizer. Following homogenization, 3 μl of 1 M spermidine solution in water was added into the lysate. The mixture was incubated on ice for 5 minutes and centrifuged for 5 minutes to precipitate the genomic DNA. The supernatant was collected and mixed with 1 volume of a 12 M LiCl solution. The sample was centrifuged for 5 minutes to precipitate the large RNA. The supernatant was filtered through a filtration column (C 6866, Sigma-Aldrich, St. Louis, Mo.) with 30 seconds of centrifugation to remove carry-over particulates.

The flow-through was mixed with 1.25 volumes of 100% ethanol and the mixture was applied to a silica filter binding column (C6991, Sigma-Aldrich, St. Louis, Mo.). The column was washed once with 300 μl of 12 M LiCl and twice with 500 μl of an alcohol wash solution comprising 80% ethanol and 10 mM tris (pH 7.0). The column was dried and bound nucleic acids were eluted in 50 μl of RNase-free water. The binding, washing, column drying, and eluting steps were assisted by a short centrifugation (30 seconds or 1 minute). All centrifugation steps were carried out at top speed (14,000×g) at room temperature. The sample was analyzed by reading the UV absorbance in a spectrophotometer and resolving 0.5 μg of each sample on a 4% agarose gel.

The yield was 4.5 μg, and the $A_{260/280}$ ratio was 2.1. Only a single band of small RNA with a mobility similar to a tRNA standard (70-80 nucleotides) was detected on the agarose gel. No genomic DNA or large RNA bands were detectable. The results demonstrate that spermidine may be used as an ionic additive to remove genomic DNA when biological samples are lysed under high pH conditions.

Example 4

Purification from Mammalian Culture Cells a) HeLa Cell Adherent Culture

HeLa cells were cultured in a T125 flask in DMEM medium with 10% FBS to near 100% confluence. Cells were detached from the flask with a trypsin/EDTA solution and then diluted in culture medium. Aliquots, each containing about 3 million cells, were prepared and the medium was subsequently removed by centrifugation. The cell pellet samples were flash-frozen in liquid nitrogen and stored at −70° C. before use. One of the frozen cell samples was lysed for 5 minutes at room temperature in 500 μl of a lysis solution comprising 3 M guanidine hydrochloride, 6 M LiCl, 25 mM EDTA, 0.75% Tween 20, and 1% 2-mercaptoethanol, pH 3.5. The lysis solution was prepared by combining 0.5 volumes of a basal solution (6 M guanidine hydrochloride, 50 mM EDTA, 1.5% Tween 20, pH 3.5) with 0.5 volumes of a 12 M LiCl solution and 0.01 volume of 2-mercaptoethanol. The sample was then centrifuged for 6 minutes to precipitate large RNA and genomic DNA. The supernatant was filtered through a filtration column (C6866, Sigma-Aldrich, St. Louis, Mo.) to remove carry-over particulates. Two volumes of 100% ethanol were mixed with the flow-through and the mixture was applied to a silica filter binding column (C6991, Sigma-Aldrich, St. Louis, Mo.). The column was then washed twice with 500 μl of an alcohol wash solution comprising 80% ethanol and 10 mM tris at pH 7.0, and subsequently dried. Bound nucleic acids were eluted in 50 μl of RNase-free water. The binding, washing, column drying, and eluting steps were assisted by a brief centrifugation (30 seconds or 1 minute) at top speed in a microcentrifuge at room temperature. Total RNA was prepared from the other frozen cell sample with a total RNA purification kit (STRN50, Sigma-Aldrich, St. Louis, Mo.). The samples were analyzed by reading the UV absorbance in a spectrophotometer and running 0.5 μg of each sample on a 2% agarose gel.

The yields were 5 μg for the preparation of selectively isolated small RNAs and 58 μg for the preparation of total RNA. The $A_{260/280}$ ratio was 2.1 for both samples. Only a prominent band of small RNA running in front of the bromophenol blue tracking dye was detected in the preparation of small RNA on the 2% agarose gel. Two prominent bands of large RNA with mobilities much slower than a 0.5 kb DNA marker were detected in the preparation of total RNA.

b) HEK293 Cell Adherent Culture

HEK293 cells were cultured in a T25 flask in DMEM medium with 10% FBS to near 100% confluence (about 4 million cells). The culture medium was removed by aspiration and the culture was washed with 5 ml Hank's Balanced Salt Solution. Following the removal of the wash solution, the culture was lysed for 5 minutes at room temperature in 750 μl of a lysis solution comprising 4.9 M guanidine hydrochloride, 3.6 M LiCl, 42 mM trizma acetate, 1.4% Tween 20, and 1% 2-mercaptoethanol, pH 3.4. The lysis solution was prepared by combining 0.7 volumes of a basal solution (7 M guanidine hydrochloride, 60 mM trizma acetate, 2% Tween 20, pH 3.4) with 0.3 volumes of a 12 M LiCl solution and 0.01 volume of 2-mercaptoethanol. The lysate was then transferred to a 2-ml tube and centrifuged for 5 minutes to precipitate the large RNA and genomic DNA. The supernatant was filtered through a filtration column (C 6866, Sigma-Aldrich, St. Louis, Mo.) and the flow-through was mixed with 850 μl of 100% ethanol. The mixture was applied to a silica filter binding column (C6991, Sigma-Aldrich, St. Louis, Mo.). The column was washed once with 500 μl of 12 M LiCl and twice with 500 μl of an alcohol wash solution comprising 80% ethanol and 10 mM tris, pH 7.0, and subsequently dried. Bound nucleic acids were eluted in 50 μl of RNase-free water. The binding, washing, column drying, and eluting steps were each assisted by a brief centrifugation (30 seconds or 1 minute) at top speed in a microcentrifuge at room temperature. The sample was analyzed by reading the UV absorbance in a spectrophotometer and resolving 0.5 μg of the sample on a 4% agarose gel.

The yield was 8.4 μg, and the $A_{260/280}$ ratio was 2.0. A prominent band of small RNA with a mobility similar to a tRNA standard (70-80 nucleotides) and a few minor bands of small RNA with mobilities slightly slower than the major band of small RNA were detected. No bands of large RNA or genomic DNA were detected.

c) K562 Suspension Culture Cells

K562 cells were grown in suspension in DMEM medium to late stage. An aliquot of 2 million cells of the suspension culture was centrifuged for 4 minutes and the medium was removed. The cell pellet was lysed in 750 µl of a lysis solution comprising 4.9 M guanidine hydrochloride, 3.6 M LiCl, 42 mM trizma acetate, 1.4% Tween 20, and 1% 2-mercaptoethanol, pH 3.4. Small RNA was purified as described in the example of HEK293 adherence culture cells. The sample was analyzed by reading the UV absorbance in a spectrophotometer and running 0.5 µg of the sample on a 4% agarose gel.

The yield was 3 µg, and the $A_{260/280}$ ratio was 2.1. A prominent band of small RNA with a mobility similar to a tRNA standard (70-80 nucleotides) and a few minor bands of small RNAs with mobilities slightly slower than the major band of small RNA were detected on the 4% agarose gel. No bands of large RNA or genomic DNA were detected.

Example 5

Purification from Mammalian Tissue

Mouse liver tissue (about 40 mg) was homogenized for about 30 seconds with a rotor-stator homogenizer in 750 µl of a lysis solution comprising 4.6 M guanidine hydrochloride, 3.6 M LiCl, 39 mM trizma acetate, 1.3% Tween 20, 5% ethanol, and 1% 2-mercaptoethanol, pH 3.4. The lysis solution was prepared by combining 0.65 volumes of a basal solution (7 M guanidine hydrochloride, 60 mM trizma acetate, 2% Tween 20, pH 3.4) with 0.3 volumes of a 12 M LiCl, 0.05 volumes of ethanol, and 0.01 volume of 2-mercaptoethanol. The homogenate was incubated at room temperature for 5 minutes and centrifuged for 5 minutes at top speed at room temperature. The supernatant was filtered through a filtration column (C 6866, Sigma-Aldrich, St. Louis, Mo.) and the flow-through was mixed with 970 µl of 100% ethanol. Small RNA was then purified by the silica column procedure as described in the example of the HEK293 adherence culture cells. The sample was analyzed by reading the UV absorbance in a spectrophotometer and electrophoresing 0.5 µg of the sample on a 4% agarose gel.

The yield was 19.2 µg and the $A_{260/280}$ ratio was 2.0. Only a prominent band of small RNA with a mobility similar to a tRNA standard (70-80 nucleotides) was detected on the 4% agarose gel. No bands of large RNA or genomic DNA were detected.

Example 6

Purification from Yeast

Yeast (*S. cerevisiae*) cells were cultured in YPD medium overnight. The $OD_{600}$ of the culture was 1.54. An aliquot of the culture containing approximately $4.6 \times 10^7$ cells was centrifuged at 12,000×g for 5 minutes and the culture medium was removed. The cell pellet was resuspended in 25 µl of Working Yeast Digestion Solution (prepared freshly from Y0253 and Y0378 in 9 to 1 ratio, Sigma-Aldrich, St. Louis, Mo.). The sample was incubated at room temperature for 10 minutes to digest the cell wall. Following the digestion, the sample was lysed for 5 minutes at room temperature in 750 µl of a lysis solution comprising 5.6 M guanidine hydrochloride, 2.4 M LiCl, 48 mM trizma acetate, 1.6% Tween 20, and 1% 2-mercaptoethanol, pH 3.4. The lysis solution was prepared by combining 0.8 volumes of a basal solution (7 M guanidine hydrochloride, 60 mM trizma acetate, 2% Tween 20, pH 3.4) with 0.2 volumes of a 12 M LiCl solution and 0.01 volume of 2-mercaptoethanol. The lysate was centrifuged to precipitate the large RNA and genomic DNA and the supernatant was filtered through a filtration column as previously described. The clarified lysate was mixed with 850 µl of 100% ethanol before RNA binding. Small RNA was then purified by the silica column procedure as described in the example of the HEK293 adherence cells. The sample was analyzed by reading the UV absorbance in a spectrophotometer and running 0.25 µg of the sample on a 4% agarose gel.

The yield was 5.3 µg, and the $A_{260/280}$ ratio was 2.1. A prominent band of small RNA with a mobility similar to a tRNA standard (70-80 nucleotides) and two less prominent bands (most likely the 5S rRNA and 5.8S rRNA) with mobilities slightly slower than the major band of small RNA were detected on the 4% agarose gel. No bands of large RNA or genomic DNA were detected.

Example 7

Purification from Gram-Positive and Gram-Negative Bacteria

*Bacillus subtilis* (gram-positive) cells and *E. coli* (gram-negative) cells were cultured in LB medium overnight. The $OD_{600}$ of the cultures was 4.4 and 4.0 for *Bacillus subtilis* and *E. coli*, respectively. Aliquots of the cultures were prepared, each containing approximately $1 \times 10^9$ cells, and centrifuged at 12,000×g for 5 minutes. Following removal of the culture medium, a *Bacillus* and an *E. coli* cell pellet were each resuspended in 25 µl of Working Bacterial Digestion Solution (prepared freshly from B7934 and B7809 in 9 to 1 ratio, Sigma-Aldrich, St. Louis, Mo.). The samples were incubated at room temperature for 10 minutes to digest the cell wall. Following the digestion, each sample was lysed for 5 minutes at room temperature in 750 µl of a lysis solution comprising 5.95 M guanidine hydrochloride, 1.8 M LiCl, 51 mM trizma acetate, 1.7% Tween 20, and 1% 2-mercaptoethanol, pH 3.4. The lysis solution was prepared by combining 0.85 volumes of a basal solution (7 M guanidine hydrochloride, 60 mM trizma acetate, 2% Tween 20, pH 3.4) with 0.15 volumes of a 12 M LiCl solution and 0.01 volume of 2-mercaptoethanol. An *E. coli* cell pellet sample was also lysed with the lysis solution without prior enzyme digestion. Small RNA was then purified as described in Example 6. The samples were analyzed by reading UV absorbance in a spectrophotometer and running 0.5 µg of each sample on a 4% agarose gel.

The yields were 2.6 µg, 4.5 µg, and 3.7 µg for *Bacillus subtilis* culture, *E. coli* culture with enzyme digestion, and *E. coli* culture without enzyme digestion, respectively. The $A_{260/280}$ ratio was 2.1 in all samples. A prominent band of small RNA with a mobility similar to a tRNA standard (70-80 nucleotides) and two less prominent bands (most likely the 5S rRNA and 5.8S rRNA) with mobilities slightly slower than the major band of small RNA were detected on the 4% agarose gel. No bands of large RNA or genomic DNA were detected.

What is claimed is:

1. A method for isolating small RNA from a biological sample, the method comprising:
    a) contacting the biological sample with a chaotropic agent and a lithium salt, wherein large RNA and other macromolecules precipitate to form a debris but small RNA remains soluble, thereby forming a solution of soluble small RNA;

b) contacting the solution of soluble small RNA with a chromatographic binding matrix in the presence of at least one alcohol, such that the small RNA binds to the chromatographic binding matrix; and c) eluting the small RNA from the chromatographic binding matrix, thereby isolating the small RNA.

2. The method of claim 1, wherein contact with the chaotropic agent and the lithium salt occurs simultaneously or sequentially.

3. The method of claim 1, wherein the chaotropic agent is chosen from guanidine hydrochloride, guanidine thiocyanate, guanidine carbonate, sodium perchlorate, sodium iodide, sodium trichloroacetate, and urea.

4. The method of claim 1, wherein the lithium salt is chosen from lithium chloride, lithium acetate, lithium citrate, lithium carbonate, and lithium borate.

5. The method of claim 1, wherein the chaotropic agent is guanidine hydrochloride and the lithium salt is lithium chloride.

6. The method of claim 1, wherein the concentration of the chaotropic agent is from about 1 M to about 8 M and the concentration of the lithium salt is from about 1 M to about 8 M.

7. The method of claim 1, wherein the chaotropic agent and the lithium salt are in a solution having a pH from about 3 to about 8.

8. The method of claim 1, wherein the chaotropic agent and the lithium salt are in a solution having a pH from about 3 to about 4.

9. The method of claim 7, wherein the solution further comprises at least one agent chosen from a detergent, a buffer, a thiol-reducing agent, an antifoaming agent, and a bulking agent.

10. The method of claim 1, wherein the debris comprises precipitated large RNA molecules, genomic DNA molecules, protein molecules, and other macromolecules.

11. The method of claim 1, further comprising a centrifugation step prior to step (b) wherein the solution of soluble small RNA is separated from the debris.

12. The method of claim 11, further comprising a filtration step prior to step (b).

13. The method of claim 1, wherein the alcohol is selected from the group consisting of methanol, ethanol, propanol, isopropanol, and butanol.

14. The method of claim 1, wherein the concentration of alcohol is greater than about 50%.

15. The method of claim 1, wherein the solution of soluble small RNA is contacted with 2 volumes of 100% ethanol during step (b).

16. The method of claim 1, wherein the chromatographic binding matrix comprising the bound small RNA is washed with at least one wash solution prior to step (c).

17. The method of claim 16, wherein the wash solution is chosen from a solution comprising from about 9 M to about 12 M of a salt and a solution comprising from about 80% to about 100% of alcohol.

18. The method of claim 1, wherein the eluting of step (c) occurs in the presence of RNase-free water or RNase-free low salt buffer.

19. The method of claim 1, wherein the small RNA is chosen from miRNA, siRNA, snRNA, snoRNA, smRNA, tasiRNA, rasiRNA, tncRNA, and scnRNA.

20. The method of claim 1, wherein the small RNA is less than 200 nucleotides in length.

21. The method of claim 1, wherein the small RNA is single stranded or double stranded.

22. The method of claim 5, wherein the guanidine hydrochloride and the lithium chloride are provided in a solution have a pH from about 3 to about 4; the concentration of guanidine hydrochloride is from about 3 M to about 6 M; and the concentration of lithium chloride is from about 1.8 M to about 6 M.

23. The method of claim 22, wherein the solution of soluble small RNA is contacted with 2 volumes of 100% ethanol during step (b).

* * * * *